United States Patent
Grison et al.

(10) Patent No.: US 10,166,530 B2
(45) Date of Patent: Jan. 1, 2019

(54) USE OF CERTAIN TRANSITION METAL HYPERACCUMULATOR PLANTS FOR REDUCING ORGANIC COMPOUNDS IN A GREEN MANNER

(71) Applicants: CENTRE NATIONAL DE LA RECHERCHE SCIENTIFIQUE (C.N.R.S.), Paris (FR); UNIVERSITE DE MONTPELLIER, Montpellier (FR)

(72) Inventors: Claude Grison, Castelnau-le-Lez (FR); Vincent Escande, Montpellier (FR)

(73) Assignees: CENTRE NATIONAL DE LA RECHERCHE SCIENTIFIQUE (C.N.R.S.), Paris (FR); UNIVERSITE DE MONTPELLIER, Montpellier (FR)

(*) Notice: Subject to any disclaimer, the term of this patent is extended or adjusted under 35 U.S.C. 154(b) by 0 days.

(21) Appl. No.: 15/325,733

(22) PCT Filed: Jul. 15, 2015

(86) PCT No.: PCT/FR2015/000146
§ 371 (c)(1),
(2) Date: Jan. 12, 2017

(87) PCT Pub. No.: WO2016/009116
PCT Pub. Date: Jan. 21, 2016

(65) Prior Publication Data
US 2017/0157594 A1 Jun. 8, 2017

(30) Foreign Application Priority Data
Jul. 15, 2014 (FR) .................... 14 56805

(51) Int. Cl.
| | | |
|---|---|---|
| *B01J 23/755* | (2006.01) | |
| *C07C 29/14* | (2006.01) | |
| *C07C 29/143* | (2006.01) | |
| *C07C 29/17* | (2006.01) | |
| *C07C 201/12* | (2006.01) | |
| *C07C 253/30* | (2006.01) | |
| *B01J 37/08* | (2006.01) | |
| *B01J 21/18* | (2006.01) | |
| *B01J 35/10* | (2006.01) | |
| *C07C 29/156* | (2006.01) | |
| *C07C 33/02* | (2006.01) | |
| *C07J 1/00* | (2006.01) | |

(52) U.S. Cl.
CPC ............ *B01J 23/755* (2013.01); *B01J 21/18* (2013.01); *B01J 35/1019* (2013.01); *B01J 35/1038* (2013.01); *B01J 35/1061* (2013.01); *B01J 37/08* (2013.01); *B01J 37/082* (2013.01); *C07C 29/14* (2013.01); *C07C 29/143* (2013.01); *C07C 29/156* (2013.01); *C07C 29/17* (2013.01); *C07C 33/02* (2013.01); *C07C 201/12* (2013.01); *C07C 253/30* (2013.01); *C07C 2601/08* (2017.05); *C07C 2601/14* (2017.05); *C07J 1/007* (2013.01); *C07J 1/0011* (2013.01); *C07J 1/0022* (2013.01); *C07J 1/0059* (2013.01)

(58) Field of Classification Search
CPC ...... B01J 21/18; B01J 23/755; B01J 35/1019; B01J 35/1038; B01J 35/1061; B01J 37/08; B01J 37/082; C07C 201/12; C07C 253/30; C07C 29/14; C07C 29/143; C07C 29/156; C07C 29/17; C07C 33/02; C07C 2601/08; C07C 2601/14; C07J 1/0011; C07J 1/0022; C07J 1/0059; C07J 1/007
See application file for complete search history.

(56) References Cited

U.S. PATENT DOCUMENTS

| | | |
|---|---|---|
| 5,498,587 A | 3/1996 | Deckers et al. |
| 6,075,145 A | 6/2000 | Heveling et al. |
| 2012/0316340 A1* | 12/2012 | Grison ..................... B01J 23/06 544/318 |

FOREIGN PATENT DOCUMENTS

| | | |
|---|---|---|
| EP | 2 233 478 A1 | 9/2010 |
| WO | 02/40493 A1 | 5/2002 |
| WO | 2006/096472 A1 | 9/2006 |
| WO | 2007/083304 A2 | 7/2007 |
| WO | 2011/064462 A1 | 6/2011 |
| WO | 2011/064487 A1 | 6/2011 |
| WO | 2013/150197 A1 | 10/2013 |
| WO | 2014/016509 A1 | 1/2014 |
| WO | 2014/128283 A1 | 8/2014 |
| WO | 2015/007990 A1 | 1/2015 |
| WO | 2015/036714 A1 | 3/2015 |

OTHER PUBLICATIONS

Boldrini et al., A new route to an active form of nickel. Transfer hydrogenation of alkenes and carbonyl compounds with 2-propanol, J. Org. Chem. 1985, 50(17) 3082-3086 (Year: 1985).*
Kastner, J.R. et al., "Catalytic Ozonation of Ammonia Using Biomass Char and Wood Fly Ash," Chemosphere, vol. 75, 2009, pp. 739-744.

\* cited by examiner

*Primary Examiner* — Pancham Bakshi
*Assistant Examiner* — Mark R Luderer
(74) *Attorney, Agent, or Firm* — Young & Thompson (57) ABSTRACT

Disclosed is a method for reducing organic compounds using catalysts containing nickel (0) from metal hyperaccumulator plants. The method can be implemented in a green manner and is advantageous compared to methods using the known catalysts.

18 Claims, 2 Drawing Sheets

| Start of reaction | Reduction of plant Eco-Ni(II) | End of reaction |
|---|---|---|
| | | |

FIG. 3

USE OF CERTAIN TRANSITION METAL HYPERACCUMULATOR PLANTS FOR REDUCING ORGANIC COMPOUNDS IN A GREEN MANNER

In organic synthesis, the reductions of organic compounds form an essential part of functional transformations. They have often been linked to hydrogen capture. On the laboratory scale, the reducing agents most used are electron donors such as metals, highly reactive neutral or ionic metal hydrides, or also organometallics requiring the use of toxic solvents or which may generate peroxides. Hazardous and difficult to handle, they are rarely used in an industrial environment. The chemical industry prefers the use of dihydrogen for carrying out catalytic hydrogenation or hydrogenolysis. The limits of these reactions are clearly identified:

the hazardous nature of the experimental conditions (dihydrogen pressure, inflammability etc.) constitutes an industrial risk;

the catalytic systems are constituted by transition metals or noble metals which are becoming scarce and the cost of which is constantly increasing.

The present invention makes it possible to overcome all of these limits. It is based on a novel utilization of the ecological catalysts derived from Ni-hyperaccumulator plants, capable of being substituted for the noble or strategic metals.

These catalysts are described in particular in the applications WO 2011/064487, WO 2013/150197 and WO 2014/016509.

The catalysts are reduced in situ by reagents that are biosourced or associated with agents capable of transferring a hydride under mild conditions, without risk and without the use of dihydrogen. Chemo-, regio- and stereoselectivity are controlled.

The potential for synthesis of the green reducing agents is significant. It allows in particular the reduction of carbonyl-containing derivatives (aldehydes and ketones). The nature of the metallophytes makes it possible to control the reduction selectivity of the multifunctional systems.

Thus, if the preceding functional groups (aldehydes and ketones) are conjugated with a double bond, it is possible to control the reduction at positions 1,2 or 1,4 by adjusting the nature of the reducing agent. Examples of reducing systems are presented below. When the degree of oxidation of the Ni of plant origin is retained, it is called Eco-Ni(II). When it is reduced to the degree of oxidation 0, it is named Eco-Ni(0).

A subject of the present invention is therefore a process for the reduction of an organic compound characterized in that a metal catalyst comprising preferably less than 2% by weight of carbon, Ni (II), Ni(0) or a mixture of Ni(II) and of Ni(0) obtained by acid treatment from the ashes of a calcined Ni-hyperaccumulator plant or of a part of a calcined Ni-accumulator plant that has accumulated Ni to a concentration at least equal to 100 ppm of calcined dehydrated plant, preferably greater than 1000 ppm of calcined dehydrated plant, a metal catalyst the Ni metal of which originates from said plant without the addition of Ni originating from an origin other than said plant, is reacted with said compound and in that the reaction for the reduction of the organic compound is carried out in the presence of a hydrogen donor and in the absence of dihydrogen, hydrides, alanes, boranes, organometallics and metals with the degree of oxidation (0).

As a general rule, the foliar Ni contents of plants on standard soils usually scarcely exceeds 5 ppm of dry matter.

DETAILED DESCRIPTION OF THE INVENTION

When studying the plants of New Caledonia, the following authors classified different categories of plants which accumulate nickel according to the content of nickel found in the dehydrated plants.

L'Huillier L, Jaffré T., Wulf A. (2010) p. 86, Mines et environnement en Nouvelle-Calédonie: les milieux sur substrats ultramafiques et leur restauration [Mines and environment in New Caledonia: media on ultramafic substrates and restoration thereof], IAC Editions Paita, 2010.

The plants or species which accumulate nickel can be classified as follows:

The hemiaccumulator species have contents between 0.01 and 0.1% of Ni (100 to 1000 ppm) in the dehydrated plants, which is greater than the toxicity threshold;

The hyperaccumulator species have contents greater than 0.1% (1000 ppm) in the dehydrated plants (ex: *Geissois pruinosa*).

The hypemickelophores have contents greater than 1% in the dehydrated plants (ex: *Psychotria douarrei*).

The present invention is preferably implemented with the "hyperaccumulator" plants i.e. those comprising more than 1000 ppm of nickel in the dehydrated plants. This category also includes, in the definition of the present invention, the plants referred to as hypemickelophores.

However, the present invention can also be implemented with hemiaccumulator plants that have accumulated a content of from 100 to 1000 ppm of nickel in the dehydrated plant.

In other words, the present invention can be implemented with plants that have accumulated nickel with a content of more than 100 ppm in the dehydrated plant and preferably with plants that have accumulated nickel with a content of more than 1000 ppm in the dehydrated plant.

In the present application and the claims, the term "hyperaccumulator" plant or species, when used without clarification, represents all of the plants or species which accumulate nickel within the meaning indicated above.

A more particular subject of the present invention is a process for the reduction of an organic compound with a metal catalyst comprising Ni(0).

A more particular subject of the present invention is a process for the reduction of an organic compound characterized in that a metal catalyst comprising preferably less than 2% by weight of carbon and of Ni(0) obtained by organic acid treatment, from the ashes of a calcined Ni-hyperaccumulator plant or of a part of a calcined Ni-accumulator plant that has accumulated Ni to a concentration at least equal to 100 ppm of calcined dehydrated plant, preferably greater than 1000 ppm of calcined dehydrated plant, a metal catalyst the Ni metal of which originates from said plant without the addition of Ni originating from an origin other than said plant, is reacted with said compound.

Advantageously, the organic compound reduction reaction is carried out in the presence of a hydrogen donor and in the absence of dihydrogen, hydrides, alanes, boranes, organometallics and metals with the degree of oxidation (0).

By "metal catalyst comprising Ni(0)", is meant within the meaning of the present invention a mixture of metals in which the nickel with the degree of oxidation (0), present as the majority proportion by mass with respect to the total mass of the metals present in the mixture, is reduced prior to its use in the reduction process as described above and below.

The Ni(0) is therefore not generated in situ in the reaction medium of the reduction reaction.

By "in the absence of metals with the degree of oxidation (0)" is meant within the meaning of the present invention, that the reaction is carried out without the use of a metal capable of producing hydrogen in the reaction medium. An example of such a metal is aluminium which, used in the presence of hydrochloric acid, leads to the formation of $H_2$ which is the hydrogen-donor species.

The organic acid is selected so that it leads, by thermal decomposition, to the formation of Ni(0). Advantageously, the organic acid is also selected so that it makes it possible to enrich the mixture with Ni(II), in particular by forming a precipitates which can be isolated by filtration, in particular on a frit.

By "organic acid" is therefore meant, in the remainder of the present application, an organic acid capable of forming a complex with Ni(II), the corresponding Ni(II) complex leading, by thermal decomposition, to the formation of particles of Ni(0).

Preferably, the acid treatment is carried out with formic acid or oxalic acid.

The Ni-hyperaccumulator plants can be selected from the following genera: *Adiantum, Agatea, Alyssum, Arenaria, Argophyllum, Baloghia, Berkheya, Blepharis, Bornmuellera, Brackenridgea, Buxus, Campanula, Cardamine, Casearia, Chromolaena, Chrysanthemum, Cleidion, Cnidoscolus, Cochlearia, Dicoma, Dichapetalum, Esterhazya, Euphorbia, Geissois, Glochidion, Heliotropium, Homalium, Hybanthus, Indigofera, Juncus, Justicia, Knema, Lasiochlamys, Leucanthemopsis, Leucocroton, Linaria, Lophostachys, Luzula, Merremia, Minuartia, Mitracarpus, Myristica, Noccaea, Oncotheca, Pancheria, Pearsonia, Peltaria, Phyllanthus, Planchonella, Psychotria, Pcynandra, Rhus, Rinorea, Ruellia, Saxifraga, Sebertia, Senecio, Shorea, Solidago, Stachys, Stackhousia, Streptanthus, Thlaspi, Trichospermum, Trifolium, Trisetum, Turnera, Vellozia, Walsura, Xylosma, Garcinia, Mosiera, Ouratea, Psidium, Senecio, Rondeletia, Ariadne, Phyllomelia.*

A more particular subject of the present invention is a process as described above characterized in that the hydrogen donor is selected from an alcohol, a carbohydrate reducing agent, formic acid or a formic acid salt, a cycloalkene, an unsaturated heterocycle, phosphinic acid, a saline hydrophosphite and a silylated derivative optionally used in the presence of a Lewis acid, a nucleophile or a ligand.

Among the alcohols, isopropanol is preferred, and among the carbohydrate reducing agents, glucose is preferred. Cyclohadiene and cyclohexene are the preferred cycloalkenes. The preferred heterocycle is indoline.

Among the formic acid salts, HCOOLi, HCOONa, HCOOK, $HCOONH_4$, $HCOONHEt_3$, more particularly HCOOH and $HCOONH_4$, may be mentioned.

Examples of reduction that can be carried out according to the present invention are given hereafter in the experimental part. A preferred example is the reduction reaction of the Meerwein-Pondorf-Verley type and the transfer of hydrogen catalyzed by biosourced Eco-Ni(0).

Small quantities of catalyst are preferably used. For example it is possible to operate with a quantity of 5% of Ni or less.

A more particular subject of the present invention is a process as described above characterized in that the hydrogen donor is either an alcohol in the presence of a base or formic acid or a formic acid salt or a hydrophosphite or a saline hydrosiloxane derivative optionally used in the presence of a Lewis acid, a nucleophile or a ligand.

An even more particular subject of the present invention is a process as described above characterized in that the hydrogen donor is either isopropanol in the presence of a base or formic acid or a formic acid salt.

Table 1 below shows reactions which have been carried out with catalysts of the invention.

TABLE 1

| Substrate | Product | Reducing agent of plant origin/ conditions | Hyperaccumulator plant type |
|---|---|---|---|
| RCHO | $RCH_2OH$ | *Eco-Ni(0)/hydrotalcite or alumina | *Psychotria douarrei Geissois pruinosa Alyssum fallicinum Alyssum murale* |
| RCHO, R'NH$_2$ | $RCH_2NHR'$ | * Eco-Ni(0)/$HCOONH_4$ | *Psychotria douarrei Geissois pruinosa Alyssum fallicinum Alyssum murale* |
| RC(O)R' | RCH(OH)R' | *Eco-Ni(0)/hydrotalcite oralumina | *Psychotria douarrei Geissois pruinosa Alyssum fallicinum Alyssum murale* |
| RCH=CH—C(O)R' | $RCH_2CH_2$—CHOHR' or RCH=CH—CHOHR' | *Eco-Ni(0)/base The selectivity is closely linked to the type of base used | *Psychotria douarrei Geissois pruinosa Alyssum fallicinum* |

In the above table and hereinafter, the R and R' substituents can represent a hydrogen atom or a linear or branched alkyl radical having from 1 to 12 carbon atoms, saturated or comprising one or more alkenyl or alkynyl bonds having 2 to 12 carbon atoms, optionally interrupted by one or more oxygen, sulphur, nitrogen atoms or a functional group such as a carbonyl, a cycloalkyl radical having from 3 to 7 carbon atoms or a heterocyclic radical with 5- or 6-members comprising one or more heteroatoms selected from the oxygen, sulphur or nitrogen atoms, an optionally fused carbocyclic or heterocyclic aryl radical, the arylalkyl radicals; all these radicals being unsubstituted or substituted with one or more radicals selected in particular from the hydroxyl, nitro, nitrile radicals, the halogens, the alkoxy or alkylthio having from 1 to 4 carbon atoms, trifluoromethyl, esterified or salified free carboxy, amino, alkylamino or dialkylamino, aminoalkyl radicals.

An even more particular subject of the present invention is a process as described above for the reduction of an organic compound, characterized in that a metal catalyst comprising Ni(0) obtained by treatment with an organic acid, from the ashes of an Ni-hyperaccumulator plant, is reacted with said organic compound in the presence of an alcohol, preferably isopropanol, and of a base, preferably selected from soda, hydrotalcite and alumina. When the organic compound is an α,β-ethylenic aldehyde or an α,β-ethylenic ketone, hydrotalcite or alumina is preferably used.

An even more particular subject of the present invention is a reduction process as described above characterized in that the acid treatment of the ashes of an Ni-hyperaccumulator plant is carried out using an organic acid selected from formic acid and oxalic acid.

A subject of the present invention is also a process as described above for the reduction of an organic compound characterized in that a metal catalyst comprising Ni (0), obtained by acid treatment with an organic acid, preferably formic acid or oxalic acid, from the ashes of an Ni-hyperaccumulator plant, a metal catalyst the Ni metal of which originates from said plant, is reacted with said organic compound in the presence of a hydrosiloxane derivative, advantageously selected from 1,1,3,3-tetramethyldisiloxane and polymethylhydrosiloxane, and optionally of a Lewis acid, a nucleophile or a ligand.

An even more particular subject of the present invention is a reduction process as described above characterized in that the organic compound with which the catalyst obtained by treatment with an organic acid, from the ashes of an Ni-hyperaccumulator plant is reacted, comprises one or more functions selected from the aldehyde, ketone, imine functions, or the conjugated carbon-carbon bonds.

An even more particular subject of the present invention is a reduction process as described above characterized in that the organic compound with which the catalyst obtained by treatment with an organic acid, from the ashes of an Ni-hyperaccumulator plant is reacted, comprises one or more functions selected from the aromatic, aliphatic aldehyde functions, monosubstituted ketones, disubstituted ketones, trisubstituted ketones, aryl ketones, functionalized ketones, cyclic ketones, polycyclic ketones, imines, the carbonyl functions conjugated with carbon-carbon bonds or the conjugated carbon-carbon bonds.

An even more particular subject of the present invention is a reduction process as described above characterized in that the metal catalyst comprising Ni(0) originates from the ashes of a nickel-hyperaccumulator plant selected from *Leucotron havanensis, Psychotria clementis, Phyllanthus balgooyi, Phyllanthus serpentinus, Psychotria douarrei, Geissois pruinosa, Alyssum fallicinum* and *Alyssum murale*, advantageously *Psychotria douarrei, Geissois pruinosa, Alyssum fallicinum* and *Alyssum murale*, preferably *Alyssum murale*.

An even more particular subject of the present invention is a reduction process as described above, for the selective reduction of one of the reducible functions of an organic compound comprising several reducible functions, characterized in that the metal catalyst is constituted by Ni(0) obtained by treatment with an organic acid, from the ashes of a nickel-hyperaccumulator plant and the reaction is carried out in the presence of isopropanol and alumina or hydrotalcite.

A quite particular subject of the present invention is also a process as described above, for the reduction of an organic compound comprising an aldehyde, ketone function and a nitro, nitrile function or an alkene or alkyne bond characterized in that, by the action of the catalyst Eco-Ni (0), the aldehyde function is reduced to an alcohol function and the nitro, nitrile functions or the non-conjugated alkene or alkyne bonds are unchanged.

An even more particular subject of the present invention is a process as described above, for the reduction of an organic compound comprising one or more unsaturated carbon-carbon bonds and an aldehyde function, preferably an α,β-ethylenic aldehyde.

Advantageously, said organic compound comprising a conjugated carbonyl function is selected from the group constituted by the monoterpenes, cinnamaldehyde and derivatives thereof, and retinoids.

By "derivatives" is meant, within the meaning of the present invention, compounds the backbone of which is similar to a natural product, also comprising modifications in its structure. These modifications are for example the introduction of functional groups such as heteroatoms. For example, by "cinnamaldehyde derivatives" is meant compounds in which the aromatic ring comprises substituents instead of one or more hydrogen atoms. An example of such a compound is 4-methoxy-cinnamaldehyde.

Among the monoterpenes in which an α,β-ethylenic aldehyde or α,β-ethylenic ketone function is present, carvone, verbenone, citral, geranial, neral, 8-oxo-geranial, piperitone, pulegone and myrcenal may be mentioned for example.

Among the monoterpenes in which an aldehyde or ketone function is present, citronellal may be mentioned for example.

Among the retinoids, retinal and derivatives thereof may be mentioned. These derivatives can for example comprise a hydroxyl function on the ring with six-members.

More preferentially, the α,β-ethylenic aldehyde or ketone is selected from citral, cinnamaldehyde, pulegone, jasmone and derivatives thereof and retinal, and by the action of the Eco-Ni(0) catalyst, the aldehyde or ketone function is reduced to an alcohol function and the unsaturated carbon-carbon bond(s) is/are unchanged.

This highly selective reaction for the reduction of the single carbonyl-containing unit can for example be implemented with the plant Eco-Ni(0)/iPrOH/$Al_2O_3$ system.

An even more particular subject of the present invention is a process as described above for the reduction of an organic compound comprising an aldehyde function, preferably citronellal, or a ketone function, preferably a cyclopentanone that is substituted and functionalized for example by carboxylic ester groups, or estrone or androsterone, characterized in that by the action of the metal catalyst comprising Ni (0) obtained by acid treatment with an organic acid, preferably formic acid, or oxalic acid, from the ashes of an Ni-hyperaccumulator plant, a metal catalyst the Ni metal of which originates from said plant, with said organic compound in the presence of a hydrosiloxane derivative and optionally of a Lewis acid, of a nucleophile or of a ligand alone, the carbonyl function is reduced to an alcohol function.

An even more particular subject of the present invention is a reduction process as described above for the reduction of an organic compound comprising one or more conjugated carbon-carbon bonds and an aldehyde or ketone function, characterized in that by the reaction of the metal catalyst comprising Ni (0), obtained by acid treatment, from the ashes of an Ni-hyperaccumulator plant, with an organic acid, preferably formic acid or oxalic acid, the aldehyde function is reduced to an alcohol function and the conjugated carbon-carbon bond(s) is/are reduced.

This simultaneous reaction for the reduction of the carbonyl-containing unit and of the conjugated double bond can for example be implemented with the Eco-Ni(0)/iPrOH/$Al_2O_3$ system.

An even more particular subject of the present invention is the use as catalyst of a composition containing a metal catalyst comprising Ni(0) obtained by treatment with an organic acid, from the ashes of a calcined nickel-hyperaccumulator plant or of a part of a calcined nickel-hyperaccumulator plant that has accumulated nickel in the Ni(II) form, a catalyst the nickel of which originates from said plant, for the implementation of an organic compound reduction reaction comprising one or more functions selected from the aldehyde, ketone, imine functions.

An even more particular subject of the present invention is the use as described above, characterized in that, for the implementation of a reaction for the reduction of an organic compound comprising an aldehyde, ketone, imine, nitro function or an unsaturated carbon-carbon bond, the metal catalyst originating from the ashes of a calcined nickel-hyperaccumulator plant or a part of a calcined nickel-hyperaccumulator plant that has accumulated nickel in the Ni(II) form, is reduced to Ni(0) beforehand in the presence of an organic acid.

A subject of the present invention is also a process for the preparation (I) of a catalyst comprising Ni(0), comprising the steps of:
  (a) calcination of an Ni-hyperaccumulator plant or of a part of an Ni-hyperaccumulator plant that has accumulated Ni at least equal to 100 ppm of dehydrated plant, preferably greater than 1000 ppm of dehydrated plant in order to obtain ashes,
  (b) treatment of the ashes obtained in step (a) with an organic acid, advantageously in order to isolate a precipitate containing at least one Ni(II) salt,
  (c) heat treatment of the product obtained in step (b) in order to obtain a metal catalyst comprising Ni(0).

Step (a) for obtaining the ashes of the plant or of the plant part that has accumulated Ni can be carried out according to the method described in the patent application WO2011/064462. Advantageously, the ashes are obtained by calcination of a plant or a part of a plant that has accumulated Ni at a temperature from 250 to 500° C., more advantageously from 350 to 450° C., in particular of 400° C.

Advantageously, said Ni-hyperaccumulator plant is selected from *Leucotron havanensis*, *Psychotria clementis*, *Phyllanthus balgooyi*, *Phyllanthus serpentinus*, *Psychotria douarrei*, *Geissois pruinosa*, *Alyssum fallicinum* and *Alyssum murale*, advantageously *Psychotria douarrei*, *Geissois pruinosa*, *Alyssum fallicinum* and *Alyssum murale*. Preferably, it is *Psychotria douarrei*.

Advantageously, step (b) of treatment of the ashes makes it possible to increase the proportion of nickel in the mixture of metals initially present in the ashes. This step is advantageously carried out by bringing the ashes into contact with an organic acid capable of forming a nickel complex the solubility of which is low enough to lead to the formation of a precipitate in a given solvent.

Advantageously, said step of bringing the organic acid and the ashes into contact is carried out with formic acid or oxalic acid, preferably formic acid. Any organic acid can be used provided that it makes it possible to increase the proportion of nickel in the mixture of metals, and that the complex that it forms with the Ni(II) can be reduced to Ni(0) by thermal decomposition.

In a particular embodiment, the step of bringing into contact is carried out in organic acid in the absence of a solvent, such as water.

Said step of bringing into contact is implemented at a temperature allowing the formation of the nickel complex with organic acid. When the organic acid is formic acid, the step of bringing into contact is implemented at a temperature from 10 to 101° C., advantageously from 50 to 100° C., in particular of 90° C.

The precipitate thus obtained contains nickel in the form of the organic acid salt, such as nickel formate or nickel oxalate and of other metals that have precipitated during this step.

As the precipitate also contains organic residues, it is advantageous to separate the metal species from these residues. A method for this separation comprises dissolving the precipitate in a solvent in which the nickel(II) salt obtained in step (b) is soluble, such as water, followed by a filtration step.

The heat treatment step (c) allows the reduction of the Ni(II) salt isolated in step (b) to Ni(0).

The nature of the organic acid used is therefore very significant, in that it must allow the formation of an Ni(II) salt in step (b) capable of leading to Ni(0) by thermal decomposition in step (c). Oxalic acid and formic acid are the preferred acids as they meet this criterion. Any organic acid leading to particles of Ni(0) by thermal decomposition can however be used.

Advantageously, the heat treatment step is carried out under a neutral atmosphere, for example under a nitrogen or argon atmosphere.

When the organic acid is formic acid, the nickel salt being nickel formate, the heat treatment step is carried out under a neutral atmosphere. The heat treatment step is in particular carried out in a material capable of resisting the temperatures necessary for carrying out step (c). It is in particular paraffin derivatives.

The heat treatment step of step (c) is carried out at a temperature from 100° C. to 400° C., advantageously from 150° C. to 300° C., preferably at 240° C.

Figure 3:
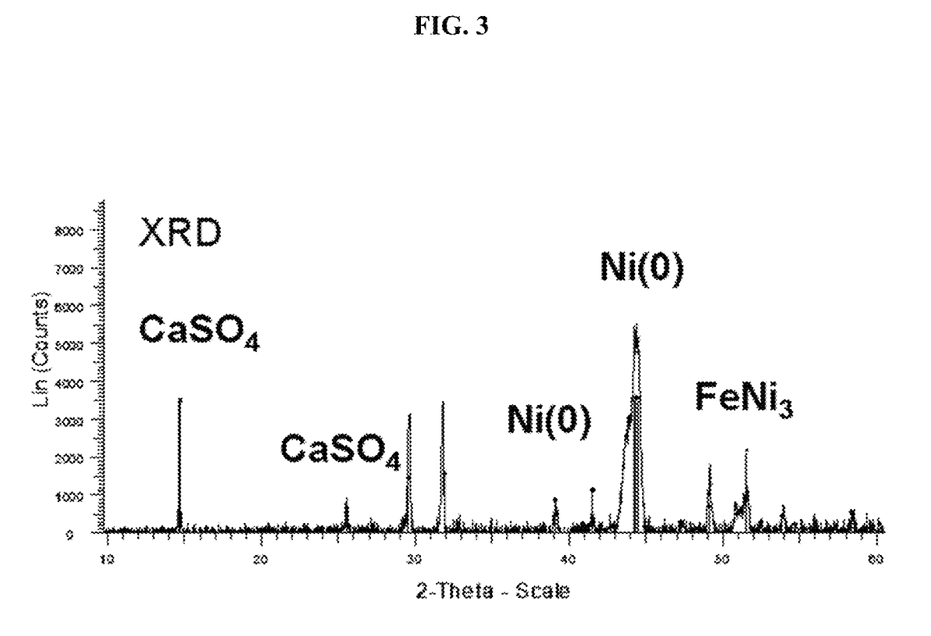
FIG. 3 shows the composition of the catalysts as determined by crystallography on the 2θ scale.

Because of the very nature of the ashes, in which a mixture of metals originating from the calcined plant is present, the metal catalyst thus obtained after heat treatment step (c) has physicochemical properties, such as specific surface area and porosity, very different from those of a catalyst obtained from the corresponding pure nickel (II) salt. The composition of the catalysts obtained is also original, as shown by the presence of a FeNi$_3$ alloy (determined by crystallography on the 2θ scale, FIG. 3).

These original physicochemical are shown by the original activity and selectivity of the catalyst in the organic compound reduction reactions (Table 1).

TABLE 1

| Substrate | Catalyst according to application WO 2011/064462 | Eco-Ni(0) catalyst | Eco-Ni(II) catalyst |
|---|---|---|---|
| Ph–CH=CH–C(O)–Ph | Complex mixture | Ph–CH$_2$–CH$_2$–CH(OH)–Ph (96%) | Degradation |

TABLE 1-continued

| Substrate | Catalyst according to application WO 2011/064462 | Eco-Ni(0) catalyst | Eco-Ni(II) catalyst |
|---|---|---|---|
| 3-nitrobenzaldehyde (CHO, NO₂) | Reduction of the nitro group | 3-nitrobenzyl alcohol (CH₂OH, NO₂) 85% | Degradation |
| bis(3-(phenylethynyl)phenyl) ketone | Reduction of the triple bond | bis(3-(phenylethynyl)phenyl)methanol (OH) 75% | — |
| citral | Complex mixture | nerol/geraniol (OH) 76/24 97% | Degradation |
| cinnamaldehyde (CHO) | mixture including cinnamyl alcohol (CH₂OH) | cinnamyl alcohol (CH₂OH) 98% | Degradation |
| β-nitrostyrene (NO₂) | phenethylamine (NH₂) 65% | 0% | 0% |

The catalyst thus obtained differs in its reactivity from the catalysts described in the application WO2011/064462, in which an Ni(II) catalyst allowed the reduction of 1-phenyl-2-nitropropene to phenylpropylamine. The catalyst according to the present invention, used in the same reaction, does not allow the reduction of this compound.

The catalyst according to the present invention therefore allows the reduction of the aldehydes, ketones and imines without the concomitant reduction of functional groups such as the nitro, non-conjugated alkene or alkyne groups.

This difference in reactivity and selectivity is also shown in the reduction of the α,β-ethylenic aldehydes and α,β-ethylenic ketones in which the catalyst according to the present invention, depending on the experimental conditions, leads the formation of allylic alcohol or saturated alcohol.

With the catalysts described in application WO2011/064462 or the Ni(II) salts obtained according to the present invention, the reduction reaction leads to the formation of a complex mixture of products or degradation products of (Table 1).

A subject of the present invention is also a process for the preparation (I-1) of a catalyst comprising Ni(0), comprising the steps of:
(a) calcination of *Psychotria douarrei*, *Geissois pruinosa*, *Alyssum fallicinum* and *Alyssum murale* or of a part of one of these plants, that has accumulated Ni at least equal to 100 ppm of dehydrated plant, preferably greater than 1000 ppm of dehydrated plant in order to obtain ashes,
(b) treatment of the ashes obtained in step (a) with an organic acid in order to isolate a precipitate containing at least one Ni(II) salt,
(c) heat treatment of the precipitate obtained in step (b) in order to obtain a metal catalyst comprising Ni(0).

A subject of the present invention is also a process for the preparation (I-2) of a catalyst comprising Ni(0), comprising the steps of:
(a) calcination of an Ni-hyperaccumulator plant or of a part of an Ni-hyperaccumulator plant that has accumulated Ni at least equal to 100 ppm of dehydrated plant, preferably greater than 1000 ppm of dehydrated plant in order to obtain ashes,
(b) treatment of the ashes obtained in step (a) with an organic acid selected from formic acid and oxalic acid in order to isolate a precipitate containing at least one Ni(II) salt,
(c) heat treatment of the precipitate obtained in step (b) in order to obtain a metal catalyst comprising Ni(0).

A subject of the present invention is also a process for the preparation (I-3) of a catalyst comprising Ni(0), comprising the steps of:
(a) calcination of *Psychotria douarrei*, *Geissois pruinosa*, *Alyssum fallicinum* or *Alyssum murale* or of a part of one of these plants, that has accumulated Ni at least equal to 100 ppm of dehydrated plant, preferably greater than 1000 ppm of dehydrated plant in order to obtain ashes,
(b) treatment of the ashes obtained in step (a) with an organic acid selected from formic acid and oxalic acid, advantageously formic acid, in order to isolate a precipitate containing at least one Ni(II) salt,
(c) heat treatment at a temperature from 100° C. to 400° C., advantageously from 150° C. to 300° C., preferably at 240° C., of the precipitate obtained in step (b) in order to obtain a metal catalyst comprising Ni(0).

In a particular embodiment, the metal catalyst is obtained by process (II) comprising the steps of:
(a) calcination of *Psychotria douarrei* that has accumulated Ni at least equal to 1000 ppm of dehydrated plant in order to obtain ashes,
(b) treatment of the ashes obtained in step (a) with formic acid, in order to isolate a precipitate containing Ni(II) oxalate,
(c) heat treatment of the precipitate obtained in step (b) at a temperature of 240° C., advantageously in paraffin, in order to obtain a metal catalyst comprising Ni(0).

The present invention also relates to a metal catalyst comprising Ni(0) obtained by the process (I), (I-1), (I-2), (I-3) or (II).

The present invention relates more particularly to a metal catalyst comprising 22% Ni(0) in the form of nanoparticles characterized by a specific surface area of approximately 109 determined using the BET method, a pore volume of approximately 0.20 cm$^3$/g and a pore size of approximately 75 Å.

The present invention also relates to a process for the reduction of an organic compound as described above, in which the metal catalyst comprising Ni(0) is obtained by the process (I), (I-1), (I-2), (I-3) or (II).

The present invention also relates to the use of a metal catalyst comprising Ni(0) obtained by the process (I), (I-1), (I-2), (I-3) or (II) for the reduction of organic compounds.

In a particular embodiment, the present invention relates to the use of a metal catalyst comprising Ni(0) obtained by the process (I), (I-1), (I-2), (I-3) or (II) for the reduction of organic compounds in the absence of dihydrogen, hydrides, alanes, boranes, organometallics and metals with the degree of oxidation (0).

The present invention relates more particularly to the use of a metal catalyst comprising Ni(0) obtained by the process (I), (I-1), (I-2), (I-3) or (II) for the reduction of organic compounds comprising at least one function selected from the aldehyde, ketone and imine functions. Advantageously, said organic compound comprises one or more functions selected from the aromatic, aliphatic aldehyde functions, monosubstituted ketones, disubstituted ketones, trisubstituted ketones, aryl ketones, functionalized ketones, cyclic ketones, polycyclic ketones, imines and the conjugated carbonyl functions.

The present invention relates particularly to the use of a metal catalyst comprising Ni(0) obtained by the process (I), (I-1), (I-2), (I-3) or (II) for the reduction of an organic compound comprising a conjugated carbonyl function, such as an α,β-ethylenic aldehyde, an α,β-ethylenic ketone or an α,β-ethylenic imine and optionally other reducible functions. Advantageously, the present invention relates to the use of a metal catalyst comprising Ni(0) obtained by the process (I), (I-1), (I-2), (I-3) or (II) for the selective reduction of an aldehyde or ketone function, of an organic compound comprising several reducible functions, such as a nitro, nitrile, non-conjugated alkene or non-conjugated alkyne group, characterized in that only the aldehyde function is reduced.

The present invention relates more particularly to the use of a metal catalyst comprising Ni(0) obtained by the process (I), (I-1), (I-2), (I-3) or (II) selected from the group constituted by the monoterpenes in which an α,β-ethylenic aldehyde or α,β-ethylenic ketone function is present, such as carvone, verbenone, citral, geranial, neral, 8-oxo-geranial, piperitone, pulegone and myrcenal, the monoterpenes in which an aldehyde or ketone function is present, such as citronellal, the retinoids, such as retinal and derivatives thereof, and the substituted cyclopentanones, such as jasmone and derivatives thereof.

More preferentially, the α,β-ethylenic aldehyde or the α,β-ethylenic ketone is selected from citral, cinnamaldehyde and derivatives thereof, jasmone and derivatives thereof, pulegone and retinal, and by the action of the catalyst Eco-Ni(0), the aldehyde or ketone function is reduced to an alcohol function and the unsaturated carbon-carbon bond(s) is/are unchanged.

The present invention is illustrated by the following examples:

EXAMPLES

The reactivity of Eco-Ni(II) was first studied.

I. Green Reduction from the Phytoextract Ni(II), Eco-Ni (II)

The principle of the process of green reduction starting from the phytoextract Ni(II), Eco-Ni (II) is based on an adaptation of the reduction of the Meerwein-Pondorf-Verley type. It can be adapted to very diverse carbonyl-containing derivatives including the hindered and functionalized ketones. The method is compatible with the presence of C—C double bonds.

Isopropanol is the preferred alcohol. The quantities of Eco-Ni involved are small but remarkably effective.

The reaction conditions are not only very effective, but also very green; they generate very little waste, use a green solvent, isopropanol, and are very easy to implement. They present no industrial risk. This method is very advantageous with respect to Raney Ni or to the metals and hydrides conventionally used. It usefully replaces the precious metals or systems that are more complex than $NiCl_2(PPh)_3$. The latter are less effective and require more Ni: the claimed Eco-Ni (II) system has a catalytic effect starting from 5% Ni, while liganded commercial $NiCl_2$ requires 15% mol. (J. Chem. Soc., Chem Comm. 1995, 465-466, S. Iyer and Jos P. Vargehese). Here, no phosphine ligand is necessary, which makes it possible to work under aerobic conditions.

The reaction described is more rapid than with the conventional systems described as being the most effective (J. Chem. Soc., Chem Comm 2000, 1647-1648, M. D. Le Page and Brian R. James). The soda can be replaced with hydrotalcite, but here the prior conditioning and activation of the hydrotalcite at a high temperature is not necessary.

Experimental Part Relating to the Green Reduction from the Phytoextract Ni(II), Eco-Ni (II)

Typical experimental protocol for the reduction of cyclohexanone by the Eco-Ni(II)/iPrOH/NaOH system:

The following are introduced into a sealed tube provided with a magnetic stirrer: Eco-Ni(II) (17 mg; 0.05 mmol Ni), isopropanol (5 mL; 65.3 mmol), NaOH (20 mg; 0.5 mmol), cyclohexanone (103.5 μL; 1.0 mmol). The reaction medium is heated at 85° C. by means of an oil bath, under stirring, for 3 hours. The composition of the reaction medium is analyzed by GC-MS, with an internal standard (biphenyl). Cyclohexanol is formed with a quantitative yield.

| Substrate R—C(O)—R' | Conditions | Reduction product RR'(CH)—OH | Yield % |
|---|---|---|---|
| cyclohexanone | Ni present in Eco-Ni(II): 6 mg (0.05 mmol Ni) iPrOH: 65.3 mmol NaOH: 4.25 mmol Substrate: 1 mmol 85° C./2 hours | cyclohexanol | 100 |
| cyclohexanone | Ni present in Eco-Ni(II): 6 mg (0.05 mmol Ni) iPrOH: 65.3 mmol hydrotalcite Substrate: 1 mmol 85° C./8 hours | cyclohexanol | 92 |
| 4-tert-butylcyclohexanone | Ni present in Eco-Ni(II): 6 mg (0.05 mmol Ni) iPrOH: 65.3 mmol NaOH: 4.25 mmol Substrate: 1 mmol 85° C./2 hours | 4-tert-butylcyclohexanol | 98 |
| cyclopentanone | Ni present in Eco-Ni(II): 6 mg (0.05 mmol Ni) iPrOH: 65.3 mmol hydrotalcite Substrate: 1 mmol 85° C./2 hours | cyclopentanol | 100 |

-continued

| Substrate R—C(O)—R' | Conditions | Reduction product RR'(CH)—OH | Yield % |
|---|---|---|---|
| acetophenone | Ni present in Eco-Ni(II): 6 mg (0.05 mmol Ni) iPrOH: 65.3 mmol NaOH: 4.25 mmol Substrate: 1 mmol 85° C./2 hours | 1-phenylethanol | 100 |
| citronellal | Ni present in Eco-Ni(II): 6 mg (0.05 mmol Ni) iPrOH: 65.3 mmol NaOH: 4.25 mmol Substrate: 1 mmol 80° C./2 hours | citronellol | 77 |
| 2-tridecanone | Ni present in Eco-Ni(II): 6 mg (0.05 mmol Ni) iPrOH: 65.3 mmol NaOH: 4.25 mmol Substrate: 1 mmol 85° C./24 hours | 2-tridecanol | 91 |
| 6-methyl-5-hepten-2-one | Ni present in Eco-Ni(II): 6 mg (0.05 mmol Ni) iPrOH: 65.3 mmol NaOH: 4.25 mmol Substrate: 1 mmol 85° C./6 hours | 6-methyl-5-hepten-2-ol | 88 |

Other hydrogen donors can be used successfully when the reaction is catalyzed by Eco-Ni(II). The hydroxylanes form part of the most effective systems.

Reduction with the Hydrosiloxanes

The hydrosiloxanes are nowadays considered as substitutes for aluminium and boron hydrides. They may be a siloxane in the strict sense of the word or a hydrosilane, or a silazane containing one or more SiH groups. They can be linear, branched or cyclic. Systems such as 1,1,3,3-tetramethyldisiloxane (TMDS) or polymethylhydrosiloxane (PMHS) are the most useful. PMHS is considered as a safe and inexpensive co-product polymer of the silicon industry. It is inexpensive, non-toxic, air- and moisture-stable. It is ideal for the development of ecologically responsible reduction processes.

Combined with transition metals, PMHS has been used successfully for the reduction of various functional groups (carbonyl-containing derivatives, acid derivatives). The nature of the hydrosiloxane-metal combination makes it possible to modulate a significant role with respect to the chemoselectivity of the reactions implemented. It has recently been shown that certain nickel salts combined with phosphine ligands could catalyze the reduction of benzaldehyde by PMHS.

The present invention shows for the first time that the catalysts derived from the nickel-hyperaccumulator plants, the Eco-Ni(II)s allow such transformations. Surprisingly, *Geissois pruinosa* leads to results superior to those of the hypernickelophore *Psychotria douarrei*.

$$R-CHO \xrightarrow[\text{ii) MeOH}]{\text{i) Eco-Ni(II), ligand, PMHS}} RCH_2OH$$

(R: aryl, alkyl group)

| Ar | Ni-hyperaccumulator plant | Treatment of the ashes | ligand | Yield* % |
|---|---|---|---|---|
| Ph | *Psychotria douarrei* | AcOH | (Cy)$_3$P | 60 |
| Ph | *Geissois pruinosa* | AcOH | (Cy)$_3$P | 73 |
| Ph | *Psychotria douarrei* | HCl | (Cy)$_3$P | 33 |

-continued

| Ar | Ni-hyperaccumulator plant | Treatment of the ashes | ligand | Yield* % |
|---|---|---|---|---|
| Ph | *Geissois pruinosa* | HCl |  | 57 |

Experimental Protocol for the Reduction of Benzaldehyde by a Hydrosiloxane: The Eco-Ni(II)/Tricyclohexylphosphine/PMHS System:

The following are introduced into a sealed tube maintained under an inert atmosphere: Eco-Ni(II) (17 mg; 0.05 mmol Ni), tricyclohexylphosphine (28 mg; 0.10 mmol), anhydrous THF (2 mL), PMHS (average $M_n$: 1700-3200) (179 µL; 3.0 mmol of hydride), benzaldehyde (101.6 µL; 1.0 mmol). The reaction medium maintained under an inert atmosphere is heated in an oil bath at 70° C. under stirring for 24 hours. After cooling down, a methanolysis is carried out by the addition of methanol (1 mL) and of a 2 M aqueous solution of sodium hydroxide (1.5 mL), then stirring at ambient temperature for 16 hours (a slight effervescence is produced). The medium is then extracted with cyclohexane then analyzed by GC-MS, with an internal standard (biphenyl). Benzyl alcohol is formed at a rate of 47% yield.

II—Preparation of Plant Ni(0), Eco-Ni(0), by Green Method and Study of its Reactivity Organic acids such as formic acid, the formic acid salts including HCOOLi, HCOONa, HCOOK, HCOONH$_4$, HCOONHEt$_3$, but also oxalic acid which is more available naturally, phosphinic acid or its sodium salt, can be used to form complexes with the hyperaccumulated salts of the nickelophores. The complexes of the transition metals mainly precipitate. The heating thereof induces the reduction of the most reducible cation, nickel. The latter has very useful physico-chemical properties; thus for example, the metallic Ni(0)-cations-anions of plant origin-formates mixture leads to a material with outstanding reducing properties.

II—Experimental Part:

Preparation of Eco-Ni (0) by Reduction of Plant Ni(II) Using Formic Acid 5 g of ashes of *Psychotria douarrei* obtained by heat treatment at 400° C. of the corresponding leaves, are dispersed in 150 mL of formic acid. The solution is stirred at 90° C. The solution becomes black fairly rapidly. After stirring for 30 hours, the reaction mixture is filtered on celite. A pale yellow solution and a grey residual solid are isolated and put aside. The solid residue deposited on the celite, composed partly of nickel formate is washed with boiling water. It is easily entrained (emerald green colour) and evaporated. 3.210 g of a light green solid is analyzed using ICP MS (Table 2). It is composed of 22% Ni. A pure catalyst would have had a level of 39%.

Figure 2:
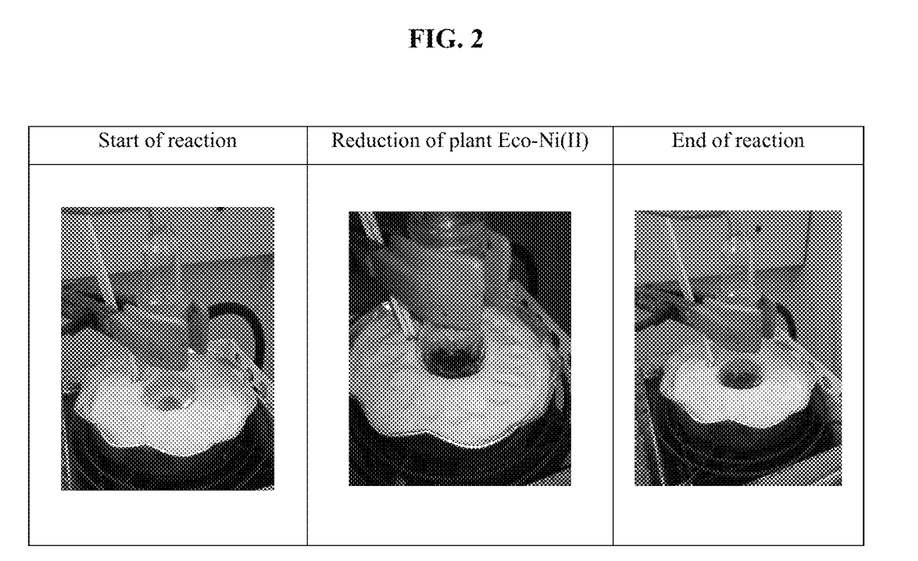
FIG. 2 describes the Reduction of the Ni formate from *Psychotria douarrei* to Eco-Ni(0).

Reduction of the Ni Formate from *Psychotria douarrei* to Eco-Ni(0) (FIG. 2).

50 mg of the preceding catalyst and 3 mL of paraffin oil (d=0.82-0.89) are introduced into a 10 mL flask. The medium is first heated at 170° C. for 1 hour using a sand bath, then at 255° C. for 4 hours under a nitrogen atmosphere. After cooling down, the mixture is filtered then washed with hexane. A fine black powder is obtained and called Eco-Ni(0). It is stored under vacuum under $P_2O_5$.

Figure 1:
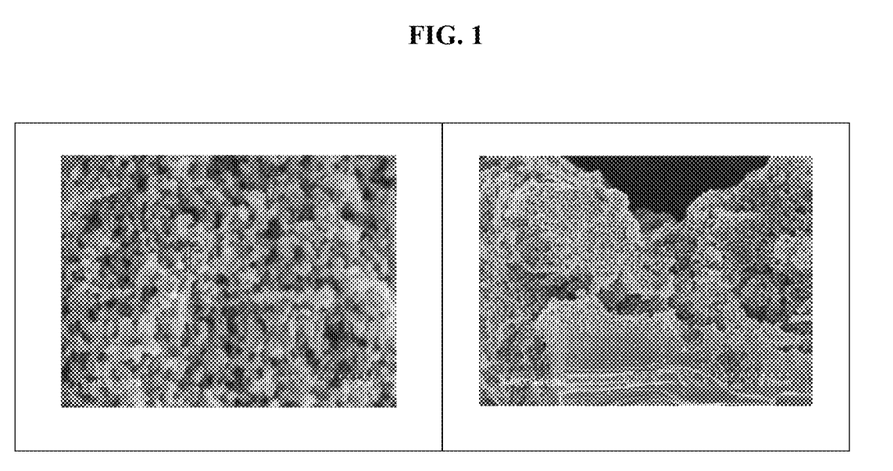
FIG. 1 shows the SEM images obtained, illustrating the porosity of the material obtained.

The solid is characterized by measuring its porosity, specific surface area and scanning electron microscope (SEM) images. FIG. 1 shows the SEM images obtained, illustrating the porosity of the material obtained.

The specific surface area measured using the BET method is 109.2621 m$^3$/g.

The volume and the size of the pores are 0.20 cm$^3$/g and 75.06 Å respectively.

The particles of nickel have an average diameter of 20 nm.

The Ni(0) of Eco-Ni(0) can be generated by an organic acid that is more available naturally, oxalic acid, or a salt of the organic acids according to the same protocol.

These methods are very advantageous. The reduction of the Ni(II) is based on an effective use of natural organic acids and therefore of renewable resources. It also avoids the use of hazardous conditions, solvents and reagents contrary to the principles of green chemistry (metal lithium, arenes such as 4,4-di-tert-butylbiphenyl, THF etc.), which are still nonetheless very often used (F. Alonso, P. Riente, M. Yus' ACCOUNTS OF CHEMICAL RESEARCH Vol. 44, No. 5, 2011, 379-391 and cited references).

Reactivity of Eco-Ni(0)

The reactivity of Eco-Ni(0) has been tested vis-à-vis different carbonyl-containing derivatives.

R = alkyl, cycloalkyl, R' = H, alkyl, cycloalkyl, aryl which can include functional groups such as C=C double bond The experimental protocol is illustrated using the example of cyclohexanone:

The following are introduced into a sealed tube provided with a magnetic stirrer: Eco-Ni(0) (1.2 mg; 0.01 mmol Ni), isopropanol (5 mL; 65.3 mmol), basic alumina (Brockmann I type) (activated beforehand by heating at 300° C. for 15 minutes) (1 g; 9.8 mmol), cyclohexanone (103.5 µL; 1.0 mmol). The reaction medium is heated at 85° C. by means of an oil bath, under stirring, for 2 hours. After cooling down to ambient temperature, the medium is filtered in order to recover the heterogeneous catalyst. The filtrate is analyzed using GC-MS, with an internal standard (biphenyl). Cyclohexanol is formed with a quantitative yield. The catalyst recovered by filtration is rinsed with isopropanol then dried in a desiccator under vacuum before being reused.

TABLE 2

| ICP-MS data ppm (mg/kg) in the solid catalyst of plant origin | | | | | | | | | | |
|---|---|---|---|---|---|---|---|---|---|---|
| Element | | | | | | | | | | |
| | $^{23}$Na | $^{24}$Mg | $^{44}$ca | $^{52}$Cr | $^{55}$Mn | $^{56}$Fe | $^{59}$Co | $^{60}$Ni | $^{65}$Cu | $^{66}$Zn | $^{88}$Sr |
| Ppm (mg/kg) | 47181 | 25189 | 30177 | 220 | 3462 | 5965 | 85 | 228030 | 121 | 158 | 341 |

The following table shows a few examples of the structures studied:

| Substrate | Conditions | Reduction product | Yield |
|---|---|---|---|
| cyclohexanone | Eco-Ni (0): 1.2 mg (0.01 mmol Ni)<br>iPrOH: 65.3 mmol<br>NaOH: 0.1 mmol<br>Substrate: 1 mmol<br>85° C./24 hours | cyclohexanol | 100 |
| cyclohexanone | Eco-Ni (0): 1.2 mg (0.01 mmol Ni)<br>iPrOH: 5 mL (65.3 mmol)<br>Al$_2$O$_3$: 1 g<br>Substrate: 1 mmol<br>85° C./18 hours | cyclohexanol | 100 |
| cyclohexanone | Eco-Ni (0): 1.2 mg (0.01 mmol Ni)<br>iPrOH: 65.3 mmol<br>Calcined hydrotalcite: 1 g<br>Substrate: 1 mmol<br>85° C./8 hours | cyclohexanol | 82 |
| cyclopentanone | Eco-Ni (0): 1.2 mg (0.01 mmol Ni)<br>iPrOH: 65.3 mmol<br>NaOH: 0.1 mmol<br>Substrate: 1 mmol<br>85° C./20 hours | cyclopentanol | 100 |
| cyclopentanone | Eco-Ni (0): 1.2 mg (0.01 mmol Ni)<br>iPrOH: 65.3 mmol<br>Al$_2$O$_3$: 1 g<br>Substrate: 1 mmol<br>85° C./18 hours | cyclopentanol | 97 |
| acetophenone | Eco-Ni (0): 1.2 mg (0.01 mmol Ni)<br>iPrOH: 65.3 mmol<br>NaOH: 0.1 mmol<br>Substrate: 1 mmol<br>85° C./24 hours | 1-phenylethanol | 100 |
| 2-butanone | Eco-Ni (0): 1.2 mg (0.01 mmol Ni)<br>iPrOH: 65.3 mmol<br>NaOH: 0.1 mmol<br>Substrate: 1 mmol<br>85° C./24 hours | 2-butanol | 100 |
| 2-tridecanone | Eco-Ni (0): 1.2 mg (0.01 mmol Ni)<br>iPrOH: 65.3 mmol<br>NaOH: 0.1 mmol<br>Substrate: 1 mmol<br>85° C./24 hours | 2-tridecanol | 91 |
| 2-tridecanone | Eco-Ni (0): 1.2 mg (0.01 mmol Ni)<br>iPrOH: 65.3 mmol<br>NaOH: 0.1 mmol<br>Substrate: 1 mmol<br>85° C./20 hours | 2-tridecanol | 86 |
| heptanal | Eco-Ni (0): 1.2 mg (0.01 mmol Ni)<br>iPrOH: 65.3 mmol<br>Al$_2$O$_3$: 1 g<br>Substrate: 1 mmol<br>85° C./20 hours | heptanol | 78 |

-continued

| Substrate | Conditions | Reduction product | Yield |
|---|---|---|---|
|  | Eco-Ni (0): 1.2 mg (0.01 mmol Ni)<br>iPrOH: 65.3 mmol<br>NaOH: 0.1 mmol<br>Substrate: 1 mmol<br>85° C./24 hours |  | 96 |
|  | Eco-Ni (0): 1.2 mg (0.01 mmol Ni)<br>iPrOH: 65.3 mmol<br>Al$_2$O$_3$: 1 g<br>Substrate: 1 mmol<br>85° C./18 hours |  | 81 |
|  | Eco-Ni (0): 1.2 mg (0.01 mmol Ni)<br>iPrOH: 65.3 mmol<br>Al$_2$O$_3$: 1 g<br>Substrate: 1 mmol<br>85° C./18 hours |  | 85 |
|  | Eco-Ni (0): 1.2 mg (0.01 mmol Ni)<br>iPrOH: 65.3 mmol<br>Al$_2$O$_3$: 1 g<br>Substrate: 1 mmol<br>85° C./18 hours |  | 83 |
|  | Eco-Ni (0): 1.2 mg (0.01 mmol Ni)<br>iPrOH: 65.3 mmol<br>NaOH: 0.1 mmol<br>Substrate: 1 mmol<br>85° C./24 hours |  | 75 |
|  | Eco-Ni (0): 1.2 mg (0.01 mmol Ni)<br>iPrOH: 5 mL (65.3 mmol)<br>Al$_2$O$_3$ 1 g<br>Substrate: 1 mmol<br>85° C./6 hours |  | 97 |

| Substrate | Conditions | Reduction product | Yield |
|---|---|---|---|
| (citronellal structure) | Eco-Ni (0): 1.2 mg (0.01 mmol Ni) iPrOH: 5 mL (65.3 mmol) Al$_2$O$_3$: 1 g Substrate: 1 mmol 85° C./4 hours | (citronellol structure) | 100 |
| (cinnamaldehyde, CHO) | Eco-Ni (0): 1.2 mg (0.01 mmol Ni) iPrOH: 5 mL (65.3 mmol) Al$_2$O$_3$ 1 g Substrate: 1 mmol 85° C./6 hours | (cinnamyl alcohol, CH$_2$OH) | 98 |
| (estrone structure) | Eco-Ni (0): 1.2 mg (0.01 mmol Ni) iPrOH: 65.3 mmol NaOH: 0.1 mmol Substrate: 1 mmol 85° C./20 hours | (estradiol structure) | 89 |

The reaction can be extended to hindered substrates, such as di- or tri-substituted ketones. In this case, the Eco-Ni(0) catalyst supported on hydrotalcite constitutes a very effective solution if R has a function susceptible to alkaline hydrolysis (e.g.: carboxylic ester group).

alkyl: C1-C6 which can include a functional group such as carboxylic alcohol, ester or acid)

The high chemoselectivity of the reduction conditions is to be noted with interest:

Aldehydes and ketones can be reduced; the high level of effectiveness of Eco-Ni(0) of plant origin contrasts with the particles of Ni(0) described in the literature. According to Alonso and Yus (Tetrahedron 64 (2008) 1847e1852), without additional ammonium formate, the benzaldehyde is reduced only to a level of 42% with the nanoparticles described in the article; the reduction of an aliphatic aldehyde is even more difficult (40%).

The only systems that make it possible to achieve this level of reducing activity originate from complex treatment using hydrides in order to reduce Ni(II) (Kidway et al., Tetrahedron Letters 47 (2006) 4161-4165). With the biosourced reducing systems that are the subject of the present application, the yields are doubled (81-85%). The other metallic species present therefore lead to an enhancement of the reducing power of the nanoparticles of Eco-Ni(0).

A carbonyl-containing derivative can be reduced in the presence of a nitro, nitrile, non-conjugated alkene and even an alkyne group. This last result shows the complementarity of selectivity with the method of Alonso and Yus which involves the reduction of the alkynes (Tetrahedron 63 (2007) 93-102).

Finally, the reduction regioselectivity of an α,β-ethylenic carbonyl-containing derivative is outstanding with plant Ni(0) in isopropanol. Contrary to the methods described (Page and James, *Chem. Commun.*, 2000, 1647-1648, Alonso et al. Tetrahedron 64 (2008) 1847-1852), in this case it is possible to very selectively reduce the single carbonyl unit with the plant Ni (0)/iPrOH/Al$_2$O$_3$ system. This possibility is illustrated with the interesting example of the controlled reduction of citral to geraniol/nerol. Citral is a very demonstrative model, since it comprises 3 different reducible sites: two C=C double bonds, one of which is conjugated, and an aldehyde function. Moreover, the reduction of citral to geraniol/nerol is of significant industrial interest in the field of the cosmetics given the rose fragrance of the geraniol/nerol mixture (Stolle et al. *RSC Adv.*, 2013.3, 2112-2153). The result obtained is very original; it is clearly different from the H$_2$/Ni/Al$_2$O$_3$ system which does not make it possible to orientate the reaction towards the controlled formation of the allyl alcohols or the hydrogenations with noble metals which lead to mixtures that are difficult to utilize.

The examples such as the reduction of citral and of cinnamaldehyde show the general applicability of the method of the present application to structures of industrial interest.

The presence of phosphine or of phosphite is not indispensable. The reactions are therefore clearly less sensitive and easy to implement.

The isopropanol can be replaced with another alcohol, such as methanol or acetic acid. In these latter cases, it is useful to introduce a formic acid salt such as ammonium formate or a phosphinic acid salt such as sodium hydrophosphite as a hydrogen reservoir. For simple reasons of solubility they are preferred to hydrazine, or to easily re-aromatizable unsaturated rings.

The invention claimed is:
1. A process for the reduction of an organic compound, comprising the following steps:
 a) preparing a metal catalyst comprising less than 2% by weight of carbon, and nickel in the form Ni(0), Ni(II) or a mixture of Ni(0) and Ni(II); said step a) comprising:
  i) calcinating a plant or part of a plant that has accumulated nickel, comprising Ni(II) in a quantity at least equal to 100 ppm of dehydrated plant, said plant being selected from the group consisting of *Adiantum, Agatea, Alyssum, Arenaria, Argophyllum, Baloghia, Berkheya, Blepharis, Bornmuellera, Brackenridgea, Buxus, Campanula, Cardamine, Casearia, Chromolaena, Chrysanthemum, Cleidion, Cnidoscolus, Cochlearia, Dicoma, Dichapetalum, Esterhazya, Euphorbia, Geissois, Glochidion, Heliotropium, Homalium, Hybanthus, Indigofera, Juncus, Justicia, Knema, Lasiochlamys, Leucanthemopsis, Leucocroton, Linaria, Lophostachys, Luzula, Merremia, Minuartia, Mitracarpus, Myristica, Noccaea, Oncotheca, Pancheria, Pearsonia, Peltaria, Phyllanthus, Planchonella, Psychotria, Pcynandra, Rhus, Rinorea, Ruellia, Saxifraga, Sebertia, Senecio, Shorea, Solidago, Stachys, Stackhousia, Streptanthus, Thlaspi, Trichospermum, Trifolium, Trisetum, Turnera, Vellozia, Walsura, Xylosma, Garcinia, Mosiera, Ouratea, Psidium, Senecio, Rondeletia, Ariadne* and *Phyllomelia*, and obtaining ashes from the calcination;
  ii) treating the ashes obtained at the end of step ii) with an organic acid selected from the group consisting of formic acid, oxalic acid and phosphinic acid, and obtaining a product from the acid treatment;
  iii) heating treating the product obtained at the end of step ii) and obtaining a metal catalyst comprising Ni(0), the Ni metal of which originating only from said plant or part of plant listed in step i); and
 b) reducing an organic compound in the presence of a hydrogen donor, and in the presence of the metal catalyst obtained from step a),
  wherein the organic compound comprises one or more functions selected from the group consisting of aldehyde, ketone, imine functions and conjugated carbon-carbon bonds; and
  wherein the hydrogen donor is selected from the group consisting of an alcohol, a carbohydrate reducing agent, formic acid or a formic acid salt, a cycloalkene, an unsaturated heterocycle, phosphinic acid and a saline hydrophosphite.

2. The process according to claim 1, wherein the reduction reaction of the organic compound is carried out in the absence of dihydrogen, hydrides, alanes, boranes, organometallics and metals with the degree of oxidation (0) as hydrogen donor.

3. The process according to claim 1, wherein the hydrogen donor is selected from the group consisting of an alcohol in the presence of a base, formic acid, a formic acid salt and a hydrophosphite.

4. The process according to claim 1, wherein the hydrogen donor is selected from the group consisting of isopropanol in the presence of a base, formic acid and a formic acid salt.

5. The process according to claim 1, wherein the hydrogen donor is an alcohol in the presence of a base.

6. The process according to claim 1, wherein the organic compound comprises one or more functions selected from the group consisting of aromatic aldehyde, aliphatic aldehyde, monosubstituted ketone, disubstituted ketone, trisubstituted ketone, aryl ketone, functionalized ketone, cyclic ketone, polycyclic ketone, imine functions, carbonyl functions conjugated with carbon-carbon bonds or conjugated carbon-carbon bonds.

7. The process according to claim 1, wherein said plant is selected from the group consisting of *Psychotria douarrei, Geissois pruinosa, Alyssum fallicinum* and *Alyssum murale, Leucotron havanensis, Psychotria clementis, Phyllanthus balgooyi*, and *Phyllanthus serpentinus*.

8. The process according to claim 1, wherein the reduction is the selective reduction of one of the reducible functions of an organic compound comprising several reducible functions, and wherein the reaction is carried out in the presence of isopropanol and alumina or hydrotalcite.

9. The process according to claim 1, wherein the reduction is the reduction of an organic compound comprising one or more $\alpha,\beta$-ethylenic aldehyde or $\alpha,\beta$-ethylenic ketone functions, and wherein the aldehyde or ketone function is reduced to an alcohol function and the unsaturated carbon-carbon bond(s) is/are unchanged.

10. The process according to claim 1, wherein the reduction reaction is carried out in the presence of isopropanol and alumina or hydrotalcite.

11. The process according to claim 1,
 wherein the organic compound is selected from the group consisting of monoterpenes in which an $\alpha,\beta$-unsaturated aldehyde or $\alpha,\beta$-unsaturated ketone function is present, monoterpenes in which an aldehyde or ketone function is present, retinoids, such as retinal and derivatives thereof, substituted cyclopentanones, and substituted cyclopentenones.

12. The process according to claim 1, wherein the hydrogen donor is selected from the group consisting of an alcohol in the presence of a base, formic acid, a formic acid salt, and a hydrophosphite.

13. The process according to claim 1, wherein the plant that has accumulate nickel comprises Ni(II) in a quantity at least equal to 1000 ppm of dehydrated plant.

14. The process according to claim 1, wherein the hydrogen donor is $HCOONH_4$.

15. The process according to claim 1, wherein the hydrogen donor is isopropanol, in the presence of a base selected from the group consisting of soda, hydrotalcite and alumina.

16. The process according to claim 1, wherein said plant is selected from the group consisting of *Psychotria douarrei, Geissois pruinosa, Alyssum fallicinum* and *Alyssum murale*.

17. The process according to claim 1, wherein said plant is *Alyssum murale*.

18. The process according to claim 1, wherein the reduction is for the reduction of an organic compound selected from the group consisting of citral, cinnamaldehyde and pulegone.

* * * * *